(12) United States Patent
Kanipayor et al.

(10) Patent No.: US 8,373,861 B2
(45) Date of Patent: Feb. 12, 2013

(54) SYSTEM FOR RAPID ANALYSIS OF MICROBIOLOGICAL MATERIALS IN LIQUID SAMPLES

(75) Inventors: Ravi Kanipayor, London (CA); Ron Emburgh, Mississauga (CA)

(73) Assignee: Les Entreprises Biospec Global Solutions Inc., He Perrot (CA)

( * ) Notice: Subject to any disclaimer, the term of this patent is extended or adjusted under 35 U.S.C. 154(b) by 605 days.

(21) Appl. No.: 11/122,089

(22) Filed: May 5, 2005

(65) Prior Publication Data

US 2005/0266516 A1    Dec. 1, 2005

Related U.S. Application Data

(60) Provisional application No. 60/569,531, filed on May 11, 2004.

(51) Int. Cl.
 *G01N 21/00* (2006.01)
 *C12M 1/38* (2006.01)

(52) U.S. Cl. .................. 356/440; 435/288.1; 435/286.1; 356/442; 356/246

(58) Field of Classification Search .................. 356/437, 356/432, 436, 440; 435/288.7
See application file for complete search history.

(56) References Cited

U.S. PATENT DOCUMENTS

| | | | |
|---|---|---|---|
| 3,506,359 A * | 4/1970 | Burke, Jr. et al. | 356/328 |
| 4,301,252 A * | 11/1981 | Baker et al. | 435/303.1 |
| 4,666,853 A * | 5/1987 | Meserol et al. | 435/286.1 |
| 4,945,060 A | 7/1990 | Turner et al. | |
| 5,292,644 A | 3/1994 | Berg | |
| 5,366,873 A | 11/1994 | Eden et al. | |
| 5,427,920 A * | 6/1995 | Berndt et al. | 435/34 |
| 5,455,176 A | 10/1995 | Prevost et al. | |

(Continued)

FOREIGN PATENT DOCUMENTS

| | | |
|---|---|---|
| CA | 2291122 | 11/1998 |
| EP | 0181962 A1 | 5/1986 |

(Continued)

OTHER PUBLICATIONS

Wilson, Thomsen, Petersen, Duus, and Oliver, "Detection of 3-hydroxykynurenine in a plant pathogenic fungus", Biochemistry Journal, 2003, 371, 783-788, Great Britain.*

(Continued)

*Primary Examiner* — Gregory J Toatley
*Assistant Examiner* — Rebecca C Bryant
(74) *Attorney, Agent, or Firm* — Birch, Stewart, Kolasch & Birch, LLP

(57) ABSTRACT

A system for the rapid analysis of microbiological parameters includes a specimen container for containing a liquid sample, a housing having an enclosable chamber shaped for receiving the specimen container, an incubating system mounted within the housing for incubating microbiological materials within the liquid sample, and a spectrophotometer system mounted within the housing for measuring light absorbed, emitted or scattered by the liquid samples as the microbiological materials are incubated by the incubating system over time. The specimen container is filled with a liquid sample to be tested and mixed with a reagent that provides a detectable parameter, and placed inside the apparatus. The incubation system heats and maintains the temperature of the liquid sample within a preset range while the spectrophotometer system propagates light within the specimen container, and monitors and records changes in the light as the light propagates through the container. A continuous non-intrusive monitoring and recording of the test parameter is achieved as the incubation progresses. Any significant deviation of the signal output is an indication of presence of the detectable parameter, while the time taken to reach the significant deviation provides quantification of the microbiological parameter under investigation.

12 Claims, 14 Drawing Sheets

U.S. PATENT DOCUMENTS

| | | | |
|---|---|---|---|
| 5,972,641 | A | 10/1999 | Øfjord et al. |
| 6,096,272 | A | 8/2000 | Clark et al. |
| 6,165,742 | A | 12/2000 | Øfjord et al. |
| 6,197,576 | B1 | 3/2001 | Eden |
| 6,372,485 | B1 | 4/2002 | Clark et al. |
| 6,465,242 | B1 * | 10/2002 | Kanipayor et al. ......... 435/288.1 |
| 6,791,689 | B1 * | 9/2004 | Weckstrom .................. 356/437 |
| 7,115,384 | B2 | 10/2006 | Clark et al. |
| 7,427,501 | B2 * | 9/2008 | Bachur et al. ............. 435/287.3 |
| 2001/0051355 | A1 | 12/2001 | Tryland et al. |
| 2002/0159066 | A1 | 10/2002 | Berstis |
| 2002/0163641 | A1 | 11/2002 | Shroder |
| 2003/0203422 | A1 | 10/2003 | Edberg |
| 2004/0121424 | A1 | 6/2004 | Richardson Casella et al. |
| 2004/0126836 | A1 | 7/2004 | Lorentzen et al. |
| 2005/0219526 | A1 * | 10/2005 | Peng ............................ 356/338 |

FOREIGN PATENT DOCUMENTS

| | | |
|---|---|---|
| EP | 0 682 244 | 11/1995 |
| WO | WO-98/53301 | * 11/1998 |
| WO | WO 03/042351 | 5/2003 |
| WO | WO 03/052126 | 6/2003 |

OTHER PUBLICATIONS

Finlayson, Spectroscopic Techniques, Analytical Chemistry and the LC Syllabus: Part 2 Applications, Proceedings ChemEd-Ireland 1996, University of Limerick.*

Samset, Ingunn Dale, et al., Colifast, Development of a surveillance system for water treatment processes and hygienic quality of drinking water, Platform presentation at "Drikkevannsforskning mot ar 2000" (Drinking water research towards year 2000)_, Trondheim, Norway Jan. 5-7, 2000.

Hussain, M,, et al., Developing a Rapid Bacteria Test for Drinking Water, Mar. 5, 2002.

Clark, James A. et al., Evaluation of Commercial Presence-Absence Test Kits for Detection of Total Coliforms, *Escherichia coli*, and Other Indicator Bacteria, Applied and Environmental Microbiology, Feb. 1993, p. 380-388.

Edberg, Stephen C., National Field Evaluation of a Defined Substrate Method for the Simultaneous Enumeration of Total Coliforms and *Escherichia colil* from Drinking Water: Comparison with the Standard Multiple Tube Fermentation Method, Applied and Environmental Microbiology, Jun. 1988, p. 1595-1601.

PCT International Searching Authority, Written Opinion dated Feb. 1, 2006, pp. 1-6, in connection with PCT/CA2005/000686.

Seres UK, Coliforms, Colilert 3000 from website http://www.seres-uk.com/colilert_3000.htm, dated 2001.

* cited by examiner

DATA TABLE

| Time | Temp | Colour | Turbidity | Flourescence | Battery | Vdd | PWM |
|---|---|---|---|---|---|---|---|
| 0.1.0 | 23.8 | 434 | 26 | 66 | | | |
| 0.3.0 | 24.0 | 428 | 26 | 66 | | | |
| 0.5.0 | 24.4 | 427 | 26 | 66 | | | |
| 0.7.0 | 24.9 | 426 | 27 | 66 | | | |
| 0.9.0 | 25.3 | 427 | 27 | 66 | | | |
| 0.11.0 | 25.9 | 430 | 27 | 66 | | | |
| 0.13.0 | 26.5 | 432 | 27 | 66 | | | |
| 0,15.0 | 26.9 | 435 | 27 | 67 | | | |
| 0.17.0 | 27.3 | 440 | 28 | 66 | | | |
| 0.19.0 | 28.1 | 442 | 28 | 67 | | | |
| 0.21.0 | 28.5 | 446 | 29 | 67 | | | |
| 0.23.0 | 29.0 | 449 | 30 | 67 | | | |
| 0.25.0 | 29.6 | 455 | 30 | 67 | | | |
| 0.27.0 | 30.0 | 458 | 31 | 67 | | | |
| 0.29.0 | 30.5 | 461 | 31 | 68 | | | |
| 0.31.0 | 31.0 | 464 | 32 | 68 | | | |
| 0.33.0 | 31.5 | 467 | 32 | 68 | | | |
| 0.35.0 | 32.0 | 470 | 33 | 68 | | | |

FIG. 13

SYSTEM FOR RAPID ANALYSIS OF MICROBIOLOGICAL MATERIALS IN LIQUID SAMPLES

The subject application claims priority to U.S. provisional application Ser. No. 60/589,531 filed 11 May, 2004.

FIELD OF THE INVENTION

This invention relates to methods and apparatus for detecting the presence and enumeration of microbiological materials in liquid samples, and in particular, to methods and apparatus for the quantitative analysis of pathogenic microbes in water samples.

BACKGROUND OF THE INVENTION

Drinking water and recreational water (water at beaches and other swimming facilities) should be tested on a regular basis, and the test results should be made available within a short period of time, in order to protect the public from harmful and contagious diseases.

Currently, most water sample tests are carried out in a laboratory environment away from water facilities or locations. Many methods and procedures currently used in routine microbiological analysis were developed over 100 years ago. They are labor intensive and time-consuming procedures both in operation and data collection. The results of such tests are typically not made available to the operators of these facilities for about 36 to 72 hours. Consequently, it is often not possible for operators of water facilities to take action to correct tainted water until long after the tainted water has been consumed or used.

In addition, the transmission of water-borne diseases remains a major concern despite worldwide attempt to curb the problem. This problem is not confined to developing and under developed countries but is global in nature. Some key reasons for this are:
(1) The current testing frequencies are not sufficient to provide early warning so that corrective action can be taken to prevent outbreak of diseases; and
(2) The current testing methods are laborious and time consuming and hence discourage frequent testing.

In 1988, Edberg S. C., et al. developed a new technology based on a chemically defined substrate MTF method known as 'Autoanalysis Colilert (AC): "National filed evaluation of a defined substrate method for the simultaneous evaluation of total coliforms and *Escherichia coli* from drinking water comparison with standard multiple tube technique', Appl. Environ. Microbiol., 54 1595 (1988)." This allowed the simultaneous detection and identification of both total coliforms and *E. coli* in water at 1 CFU per 100 mls in less than 24 hours. The Colilert®, a chromogenic-fluorogenic reagent medium, provided the specific nutrients, and enzyme substrates with chromophores and fluorophores for the simultaneous detection of total coliform and *E. coli*. In 1989, the US EPA approved this method as a means of qualitative testing of total coliform in drinking water.

The development of chromogenic/fluorogenic reagents to conduct microbial testing has opened the door to better and faster testing protocols. In addition, these products provide the additional opportunity to use technology such as optical spectroscopy to conduct biological, microbiological and chemical analysis. Spectrophotometric analyses are very sensitive and hence can detect the presence of a very low concentration of color producing components of interest in liquid samples (in parts per million). Visually, the human eye can only detect the color when these components are present in very high concentration, thus the need for incubation periods ranging from 18 to 72 hours. The time required to identify or estimate the presence of microbiological indicators in water, food and environmental samples can be drastically reduced when combining incubation with photometric analysis.

The use and advantage of spectrophotometric application to microbial analysis in liquid samples have been cited in the literature. However, the tests have been done outside the incubation chamber by drawing an aliquot of a sample from the incubation vessel to photometric tubes at various intervals and measuring using standard spectrometers. This is not only time consuming but requires separate incubators, spectrometers and technical personnel to conduct the test and in some cases robotic sampling systems. There is also a potential risk of cross contamination and human error, if proper care is not applied in conducting the analysis.

Accordingly, there is an urgent need for improved methods and apparatus for testing microbiological materials in drinking water, recreational water and wastewater, to provide better management of water facilities and to protect public health and the environment.

SUMMARY OF THE INVENTION

The present invention relates to a system for the rapid quantitative analysis of bacteria in fluid samples such as water. One aspect of the present invention is a system comprising a specimen container for containing a test sample and an apparatus having a spectrophotometer system comprising an appropriate light emitting source and a detector proximate to the specimen container within the housing of the apparatus. A reagent that provides a detectable parameter (e.g., color, fluorescence etc.) is added to the test sample in the specimen container. While the sample undergoes incubation, the detector monitors the light from the source passing through the sample and the specimen container. The detector is connected to a spectrophotometer processor that measures, processes, records and stores the information. The processor can also be connected to an appropriate measuring and recording device such as a computer, multimeter or any other device, which can measure, and record the output signal from the detector. This provides a non-intrusive continuous incubation and signal growth measurement of the parameter under investigation.

Another aspect of the present invention is a system for the rapid analysis of microbiological parameters in liquid samples. The system comprises a specimen container for containing the liquid sample, the specimen container being made from a material that allows for the propagation of light, a housing defining an enclosable chamber for holding the specimen container, an incubating system mounted within the housing for incubating microbiological materials within the liquid sample, and a spectrophotometer system mounted within the housing for propagating light within the specimen container and measuring light absorbed, emitted or scattered by the liquid sample as the microbiological materials are incubated by the incubating system over time.

A further aspect of the present invention is an apparatus for detection of microbiological materials in a liquid sample. The apparatus comprises a housing having an enclosable chamber shaped for holding a clear plastic container for containing a liquid sample, incubating apparatus mounted within the housing for incubating any microbiological materials within the liquid sample, and spectrophotometer apparatus mounted within the housing for measuring light absorbed, emitted or scattered by the liquid sample as the microbiological materials are incubated by the incubation apparatus over time.

The present invention is also directed to a method for the rapid analysis of microbiological materials in a liquid sample, comprising the steps of:

(a) mixing a liquid sample having an unknown initial population of a microbiological material with a reagent in a specimen container, the reagent providing a detectable parameter indicative of the microbiological material, thereby creating a sample/reagent mixture;

(b) placing the specimen container in an enclosable housing and enclosing the housing;

(c) incubating the sample/reagent mixture in the enclosed housing at a temperature within a preselected temperature range over a period of time; and (d) measuring changes in the detectable parameter as the sample/reagent mixture is being incubated during the period of time.

The present invention is further directed to a method for the rapid quantitative analysis of microbiological materials in a liquid sample. The method comprises the steps of:

(a) placing a liquid sample having an unknown initial population of a microbiological material in a specimen container made from a material that allows for the propagation of light;

(b) creating a sample/reagent mixture by mixing the liquid sample with a reagent that provides a detectable parameter indicative of the microbiological material upon exposure to light;

(c) incubating the sample/reagent mixture in an enclosed housing at a temperature within a preselected temperature range over a period of time;

(d) measuring changes in the detectable parameters as the sample/reagent mixture is being incubated by propagating light of a known intensity within the sample/reagent mixture and measuring changes in the intensity of the light over time;

(e) recording the changes in the intensity of the light as a function of time;

(f) recording a time of significant deviation at which there occurs an exponential change in the detectable parameter; and (g) determining the initial population by correlating the time of significant deviation with known times of exponential growth for the detectable parameter for known initial populations of the microbiological material.

BRIEF DESCRIPTION OF THE DRAWINGS

The invention will now be described, by way of example only, with reference to the following drawings, in which:

FIG. 13 is a test report generated by the subject method;

DETAILED DESCRIPTION OF THE INVENTION

Figure 1:
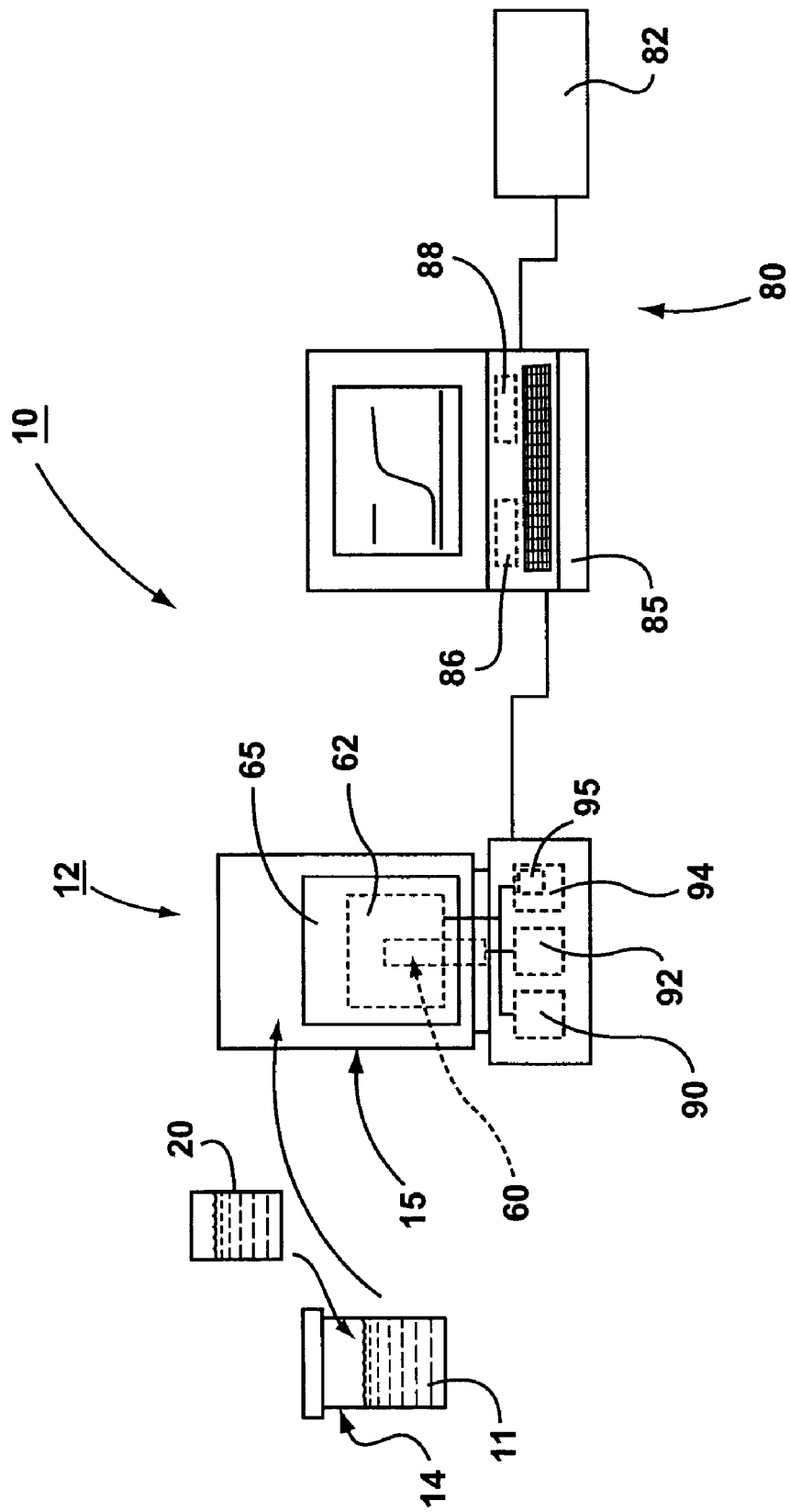
FIG. 1 is a schematic diagram of the system of the present invention.

Referring to FIG. 1, illustrated therein is a system for the rapid analysis of microbial parameters using non-intrusive in-vessel incubation and detection, made in accordance with the subject invention. The system 10 comprises an incubator-detector apparatus 12, a specimen container 14 for containing a liquid sample 11 mixed with reagent 20, and external data recorder 80. Incubator-detector apparatus 12 comprises a housing 15 having a detection chamber 65 shaped for receiving specimen container 14, an incubation system 60 mounted in housing 15 for incubating microbiological materials within liquid sample 11, and a spectrophotometer system 62 mounted in housing 15. Spectrophotometer system 62 measures the amount of light absorbed, emitted or scattered by the liquid sample 11 in specimen container 14 as microbiological materials are incubated by incubation system 60.

Incubation system 60 includes heating controller 92, and spectrophotometer system 62 includes spectrophotometer controller 94. Power source 90 provides power to incubation system 60 and spectrophotometer system 62. External data recorder 80 preferably comprises a computer 85 having a microprocessor 86 and memory device 88, and an output device such as printer 82 that is connected to computer 85.

Referring now to FIGS. 2-6, illustrated therein is a preferred embodiment of incubator-detector apparatus 12. Housing 15 of apparatus 12 is a generally cylindrical enclosure comprising a base 16, container holder 18 shaped to hold sample container 14, and a removable cap 50. Base 16 includes an upwardly extending cylindrical lip 55 shaped to receive cap 50. Base 16 houses power source 90, heating controller 92 and spectrophotometer controller 94. Power source 90 can be any suitable power source known in the art, such as a rechargeable battery located within base 16 having power outlet 99 for connection to an external 120 or 220 volt AC power source or a DC power source Mounted on the exterior of base 16 are power switch 13, status LEDs 97, and data port 98.

Container holder 18 comprises a base 21 and an open-ended cylindrical wall 19 extending upwardly from base 21. Wall 19 is shaped to surround the lower portion of specimen container 14 when specimen container 14 is placed inside housing 15. Wall 19 includes a pair of inwardly extending, diametrically opposing, generally rectangular indents 23.

Removable cap 60 is shaped to fit snugly around wall 19 of container holder 18. Cap 50 preferably comprises a thermally efficient, double wall cylindrical shell having an outer wall 51, inner wall 59, closed top 52 and open-ended bottom flange 53. The outside surface of bottom flange 53 is provided with a bead 66 shaped to thread into groove 67 on the inside surface of lip 55 of base 16. The inner surface of inner wall 59 includes a protrusion 68 shaped to sealingly engage ring 49 extending around base 21 of container holder 18. Cap 50 may optionally be provided with vacuum or inert gas between the walls 51 and 59.

When cap 50 is placed over container holder 18, cap 50 and container holder 18 define a very efficient thermally insulated incubation-detection chamber 65. The inside surface of wall 19 of specimen holder 18 is preferably blackened to make chamber 65 an efficient black box (dark room) for optical detection and measurement.

The incubation system 60 of apparatus 12 comprises heating element 24, temperature sensor 25, and incubation controller 92. Heating element 24 is mounted within heating finger 57 extending upwardly through an aperture in base 21 of container holder 18. Temperature sensor 25 is mounted inside a temperature finger 56 extending upwardly from base 21 of container holder 18. The temperature sensor 25 may comprise a thermistor 26 placed near the top of finger 56.

Heating controller 92 controls the heat to the heating element 24 and monitors the temperature of liquid sample 11 through temperature sensor 25. Once the temperature reaches the optimum, heating controller 92 maintains the temperature of liquid sample 11 within. Heating controller 92 preferably comprises a timer (not shown) for measuring the incubation time from the start and to deactivate the heating at the end of a preset time.

Specimen container 14 comprises a specimen cap 42 and a specimen bottle 44. Specimen bottle 44 is generally cylindrical with bottom cavity 45 to accommodate heating finger 57 and bottom cavity 46 to accommodate temperature sensor finger 56. Specimen bottle 44 also has a pair of diametrically opposed, generally rectangular side recesses 48 shaped to register with indents 23 of wall 19 when specimen container 14 is positioned within container holder 18. Specimen bottle 44 is made from a material that allows for the propagation of light signals, and is preferably made of a clear plastic or other material that is optically transparent.

Figure 4:
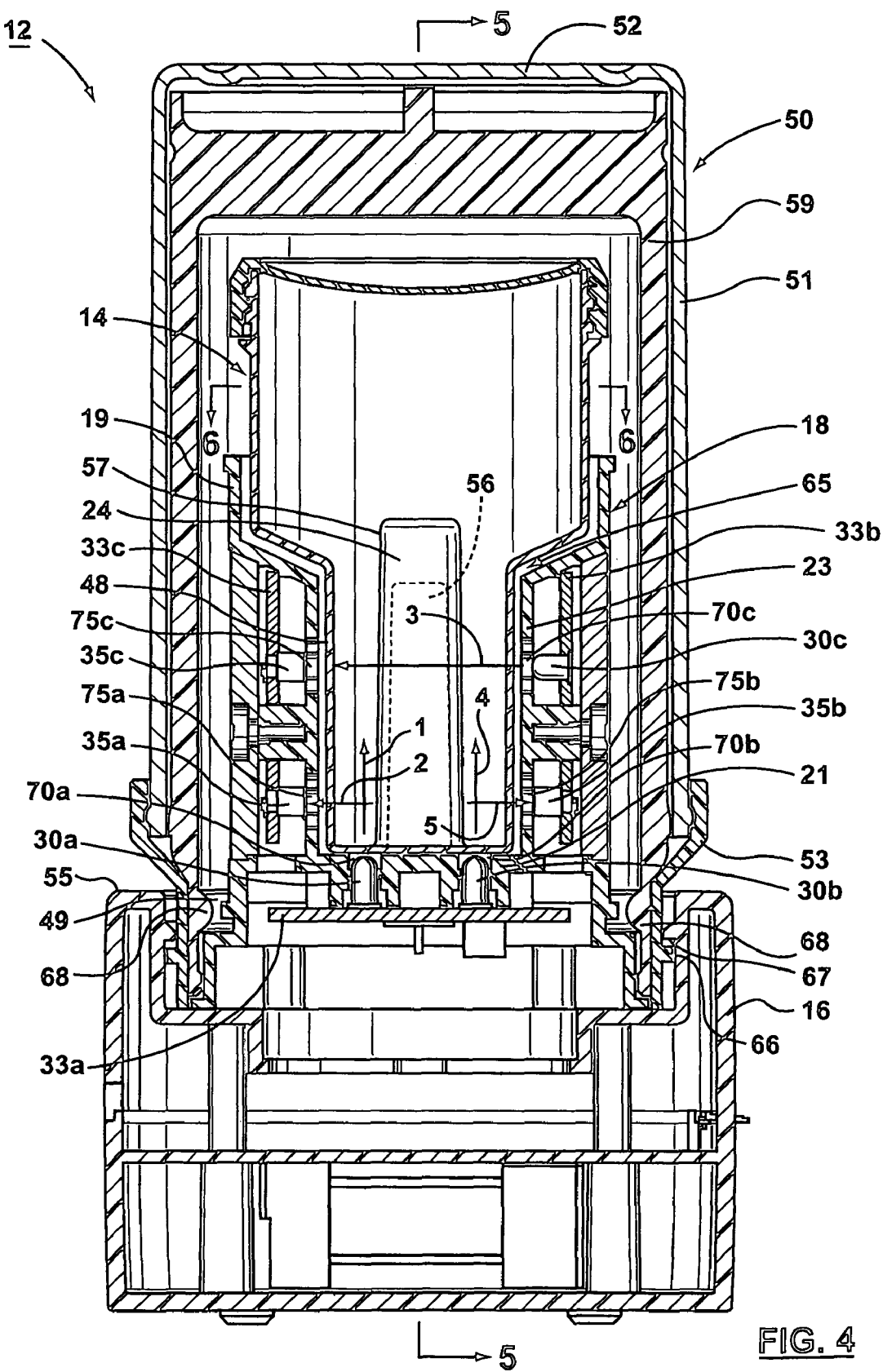
FIG. 4 is a sectional view of the subject apparatus taken along line 4-4 of FIG. 2.
Figure 5:
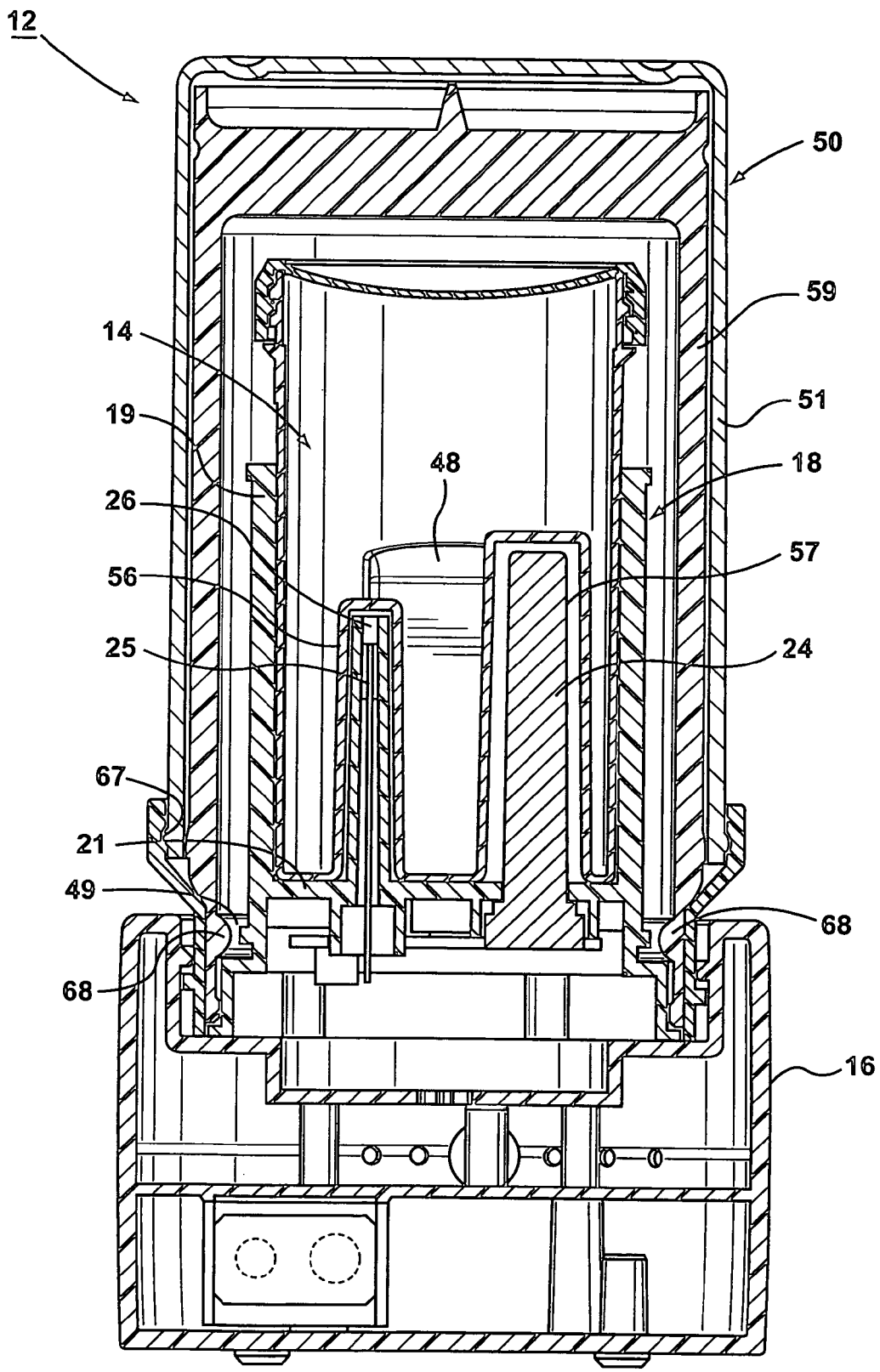
FIG. 5 is a sectional view of the subject apparatus taken along line 5-5 of FIG. 4.
Figure 6:
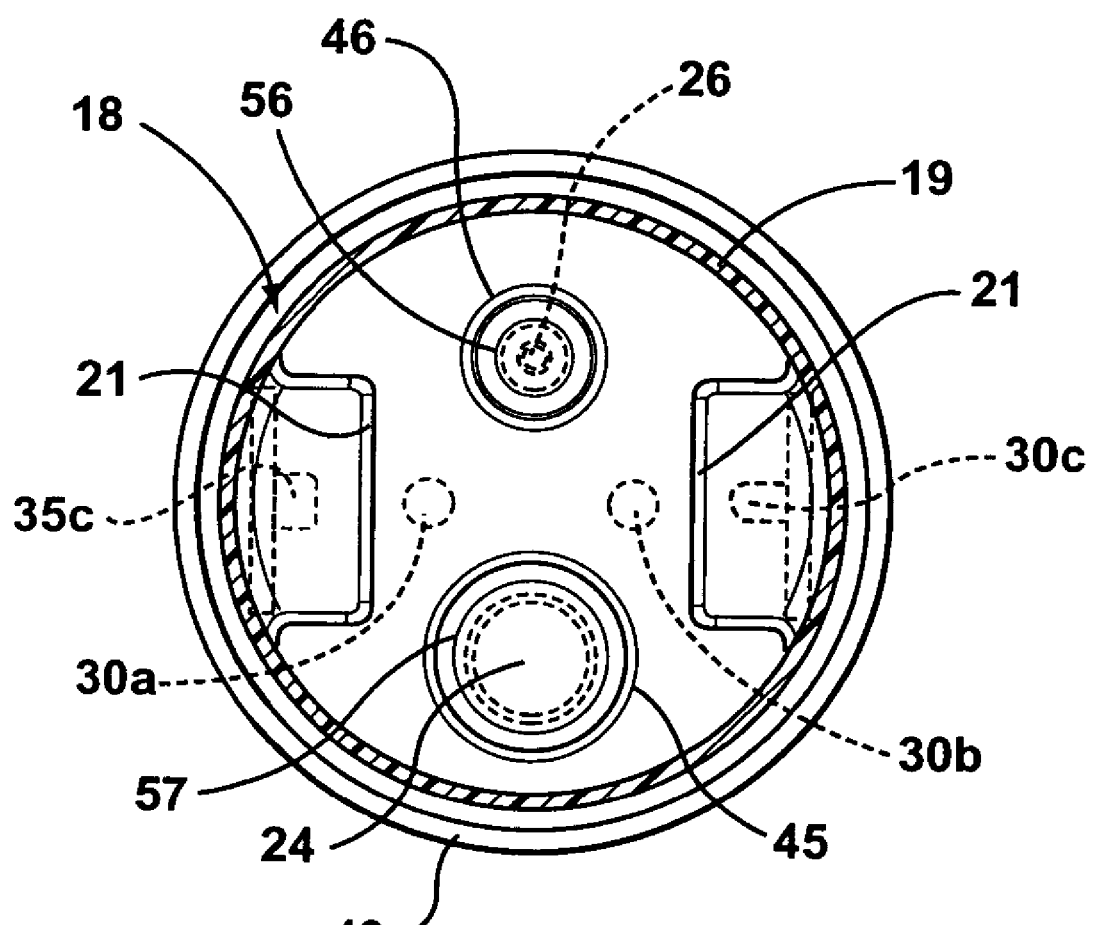
FIG. 6 is a sectional top view of the subject apparatus taken along line 6-6 of FIG. 4.

Spectrophotometer system 62 is a system for measuring light absorbed, emitted or scattered by the liquid sample as the microbiological materials are incubated over time. As best shown in FIG. 4, spectrophotometer system 62 preferably comprises three spectrophotometers, a first spectrophotometer comprising light emitting source 30a and detector 35a, a second spectrophotometer comprising light emitting source 30b and detector 35b, and a third spectrophotometer comprising light emitting source 30c and detector 35c. Light emitting sources 30a,b,c propagate beams of light of a given intensity along selected optical paths within specimen container 14. Light detectors 35a,b,c are positioned to detect changes in the intensity of the beams of light within a selected field of view related to the optical paths, resulting from light that is absorbed, emitted or scattered by the liquid sample 11 as the microbiological materials are incubated by the incubator system over time.

Each of light sources 30a,b,c preferably comprises a light emitting diode (LED) of a specific wavelength maximum, and each of detectors 35a,b,c preferably comprises a phototransistor detector. Light sources 30a,b,c and detectors 35a,b,c are mounted on printed circuit boards 33a,b,c that are electrically connected to spectrophotometer controller 94.

Light emitting sources 30a, 30b extend through apertures 70a and 70b in base of container holder 18. Light emitting sources 30a, 30b placed in such a way that the light emitting from the sources travels through apertures 70a and 70b, respectively, and upwardly along a selected optical path within specimen container 14. In the case of light emitting source 30a, 30b, the optical paths are shown by arrow 1 and arrow 4, respectively. Container holder 18 also has apertures 75a, 75b for signal detectors 35a, 35b. Detectors 35a, 35b are placed at a 90 degree angle with respect to light emitting sources 30a, 30b, in such a way that the detector window face towards specimen bottle 44 to receive any signal propagating towards detectors 35a, 35b, having fields of view shown by arrow 2 and arrow 5, respectively.

Container holder 18 also includes suitable apertures 70c and 75c for signal-emitting source 30c and signal detector 35c, respectively. Light emitting from light source 30c passes through aperture 70c along a horizontal optical path, with the direction of the propagation shown by arrow 3 through the specimen container 14 and aperture 75c to detector 35c. Detector 35c is positioned so that its field of view is at a 180° angle to the optical path of light source 30c.

Spectrophotometer controller 94 controls the operation of the spectrophotometer system. Spectrophotometer controller 94 activates and deactivates and may pulse signal emitting sources 30a,b,c. Spectrophotometer controller 94 also measures and processes the output signals generated by detectors 35a, 35b and 35c. Spectrophotometer controller 94 includes a microprocessor 95 having a built in time clock that functions as a data logger and stores the measured detector signal values along with the corresponding temperatures of the liquid sample 11 and time of the measurements in a specific memory location within microprocessor 95. Spectrophotometer controller 94 may indicate the end of the test by activating one or more of status LEDs 97 or an audio signaling device (not shown). Spectrophotometer controller 94 also communicates through data port 98 with external data recording device 80, such as computer 85, a multimeter or other external signal manipulator.

Microprocessor 95 of spectrophotometer controller 94 includes a memory for storing software that implements the test method of the subject invention. The test method provides the specifications and conditions required to conduct the testing process. Through custom software the method can be programmed and downloaded into the memory of microprocessor 95 through data port 98. The software is also capable of erasing all memory locations within the controller 94.

To utilize apparatus 12 of the present invention to test liquid samples, liquid sample 11 is placed in sample container 14. Liquid sample 11 is not limited to water, and may comprise other liquids or other liquid medium containing suspensions such as food particles, filter papers and other solids. An appropriate reagent 20 is then added to liquid sample 11 inside specimen container 14. Reagent 20 may be chemical or biological in nature and provide a detectable parameter such as color, fluorescence, turbidity etc. that indicates the presence or absence of the microbiological material under investigation.

The detection of color, fluorescent or turbidity signal is time dependent and the time of detection is related to the quantity of the bacteria present at the start of the test. Thus quantification of the detected microbial parameters such as total coliform and *E. coli* in water sample can be achieved by measuring the signal due to color change or fluorescence signal and the time at which they were detected in appreciable amount.

The detection of the color or the detection of the fluorescence signal is measured using spectrophotometer system 62 of apparatus 12. In the preferred embodiment, spectrophotometer system 62 comprises three spectrophotometers that provide colorimetric detection for total coliform, fluorescence detection for *E. coli* and microbial growth turbidity by nephelometry, respectively.

The built-in time clock of microprocessor 95 of spectrophotometer controller 94 provides the time of growth while the constant temperature of incubation system 60 provides both microbial growth and optical reproducibility.

In a preferred embodiment of system 10 of the present invention, spectrophotometer system 62 comprises three "time-of-growth-spectrophotometers" within a single constant temperature incubator, i.e. spectrophotometers that record the growth of specified microbiological parameters as a function of time. The type of spectrophotometric analysis done by each spectrophotometer depends upon the configuration and specification of the source and detector of the spectrophotometer. The 180-degree configuration of source detector pair 30c, 35c provides a colorimetric or turbidimetric analysis, while the 90-degree configuration of source-detector pairs 30a, 35a and 30b, 35b provides for either fluorometric or nephelometric analysis.

Source 30c of calorimeter spectrophotometer preferably comprises an LED with wavelength maximum at 620 nm, and detector 35c is preferably a phototransistor detector having a signal response ranging across the visible region including the 620 nm. Source 30a of fluorometer spectrophotometer is preferably an UVLED with maximum wavelength at 380 nm, and detector 35a, placed strategically at 90 degrees to source 30b, is preferably a phototransistor detector having a signal response in the visible region including the 400-500 nm range. The nephelometer configuration is similar to that of the fluorometer except that source 30b is preferably an LED with a maximum wavelength at 400 nm.

After reagent 20 is aseptically added to the sample, specimen cap 42 is fastened to specimen bottle 44, and specimen container 14 is gently shaken to dissolve the reagent, and form a sample/reagent mixture. For simultaneous testing of total coliform and E. coli in water samples, typical reagents provides not only an optimum growth nutrient, but also a color change for total coliform and fluorescence signal for E. coli, if they are present in any quantity in the sample. Examples of typical chromogenic/fluorogenic reagents are:
Merck KGaA—Readycult®
IDEXX—Colilert®

Figure 2:
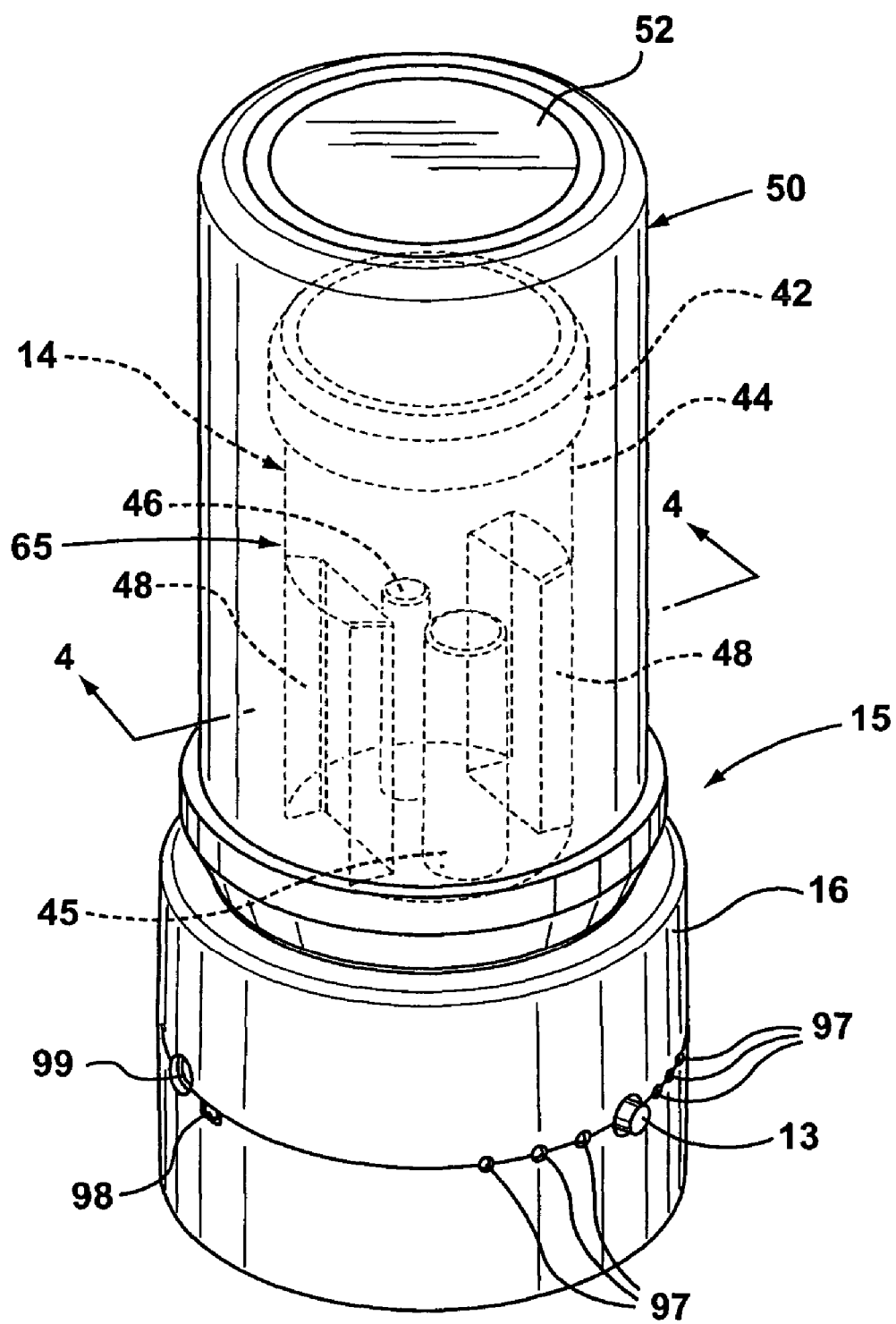
FIG. 2 is a perspective view of apparatus made in accordance with a preferred embodiment of the subject invention.
Figure 3:
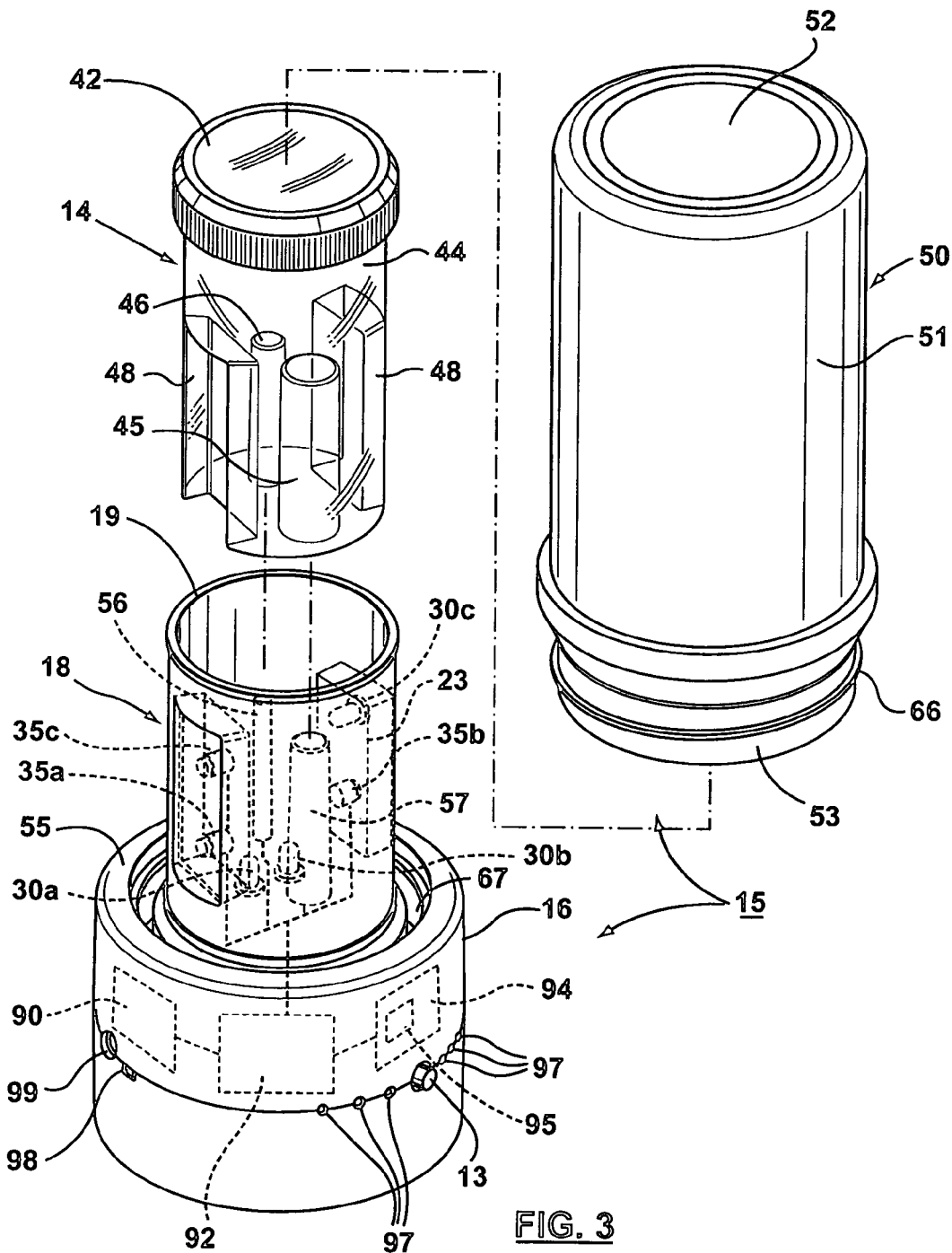
FIG. 3 is an exploded perspective view of the subject apparatus, showing the cap off and the specimen container removed from the base unit.

The specimen container 14 is then placed inside the container holder 18 as best shown in FIG. 2. Once the removable cap 50 is placed on base 16, incubation-detection chamber 65 provides a black box (dark room) condition ideal for microbial growth and spectrophotometric detection.

Pressing the start button 13 on base 16 of apparatus 12 activates the incubation cycle and the detection process. Optionally, a separated activation button can be used to activate the detection process at a pre-determined time after the start of the incubation.

Activation of the detection process may include turning the power to the signal emitting sources 30a,b,c and detectors 35a,b,c, pulsing the signal emission and monitoring the signal output of detectors 35a, b, c.

Heating controller 92 brings and maintains the temperature of liquid sample 11 at a constant temperature within a preset temperature range. For coliform and E. coli testing in water a temperature of 36±1° C. is preferred. However, the temperature depends upon the reagent used and may vary from one reagent to another. The temperature also depends upon the test method specification. For example, E. coli can be tested at either 36° C. or 41° C. using the same reagent.

Spectrophotometer controller 94 continuously monitors, records and stores the output signals from the detectors 35a, b,c. In the method of the preferred embodiment, spectrophotometer controller 94 also records and stores the time and temperature of each output signal. Controller 94 may be connected to external data recorder 80 that is programmed to record the signal either continuously or at a pre determined intervals. External data recorder 80 may also record the time of each signal measured and the corresponding temperature of the sample, and generate a "time dependent growth signal pattern" (TDGSP) of the microbial parameters under investigation.

The calorimetric TDGSP of total coliform and fluorometric TDGSP of E. coli are preferably recorded simultaneously along with a nephelometric TDGSP of increasing turbidity due to bacterial growth in water.

A significant deviation of the output signal from the initial base line is an indication of the presence of the parameter under investigation while the time needed to reach the significant deviation from the start provides an indication of the original amount of the test parameter.

The time clock of microprocessor 95 provides the date and time test started, the time of each measured signal and the corresponding temperature, the time at which the test completed or terminated. The end of the test can be indicated through status LEDs 97 and/or audio signals or can be controlled through a software program.

Figure 7:
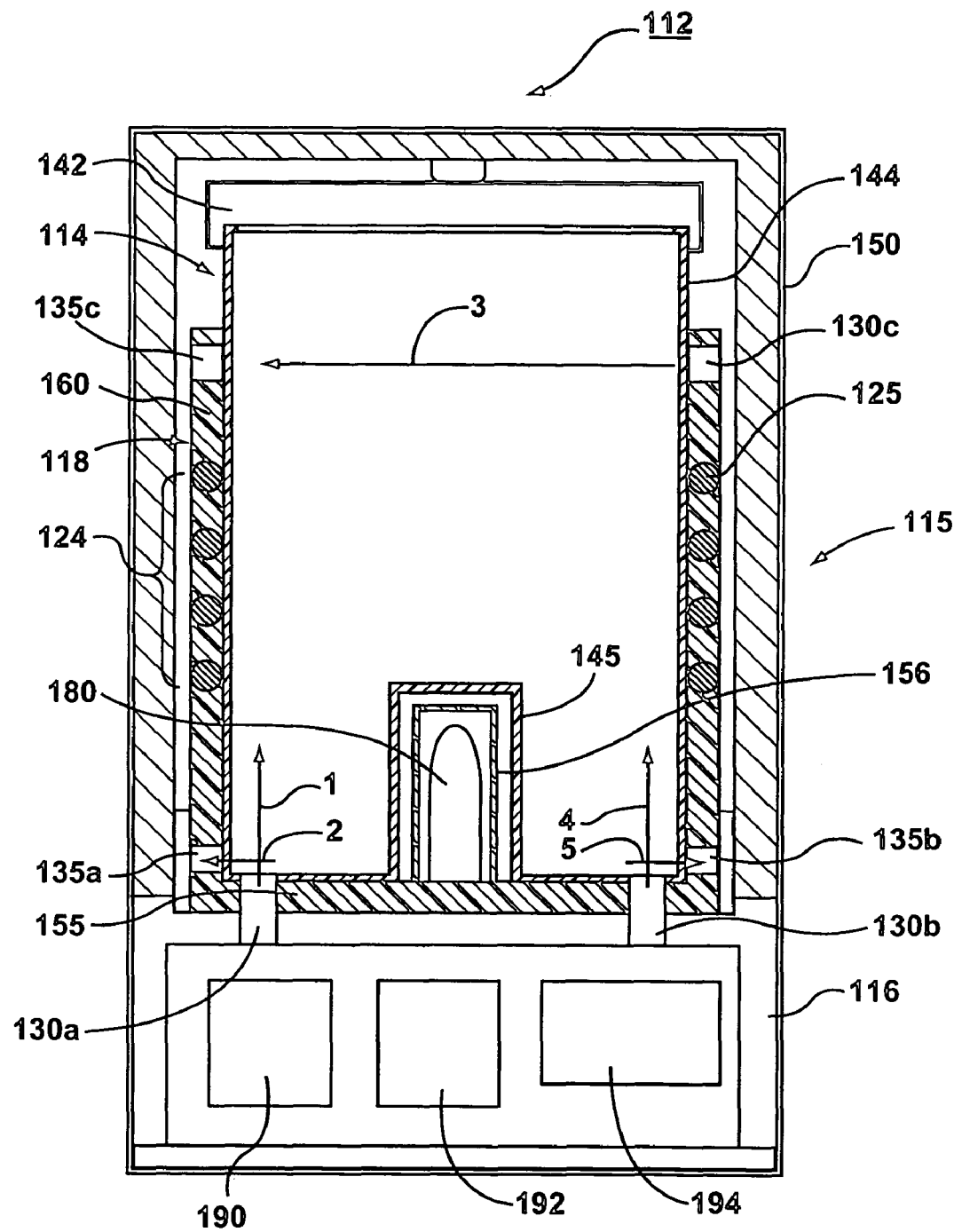
FIG. 7 is a sectional front view of an apparatus made in accordance with an alternative embodiment of the present invention.

Referring now to FIG. 7, illustrated therein is a schematic view of apparatus 112 made in accordance with an alternative embodiment of the present invention. Apparatus 112 is generally similar to apparatus 12 of the preferred embodiment as shown in FIGS. 2-6 except for a few modifications.

Apparatus 112 comprises a specimen container 114, and a housing 115 comprising a base 116, a cylindrical container holder 118, and a removable cap 150. Container holder 118 has a cylindrical base 155 and an open-ended cylindrical wall 160. Container holder base 155 has a temperature controller finger 156 extending upwards to accommodate temperature controller 180. Temperature controller 180 may be a bimetal switch or any other suitable device, which can activate and deactivate the heating element.

A heating element 124 is mounted within the open ended cylindrical wall 160 of the sample holder 150. As shown, heating element 124 comprises a resistor wire 125. Alternatively, heating element 124 may be a resistor coil, resistor foil etc. The length of the resistor wire is dictated by the resistor temperature and the ohm per foot rating of wire 125.

Specimen container 114 comprises a specimen cap 142 and a specimen bottle 144. The specimen bottle is generally cylindrical with a bottom cavity 145 shaped to accommodate temperature controller finger 156.

Heating controller 192 maintains a constant preset temperature range within the sample. Optionally it may comprise a timer (not shown) for measuring the incubation time from the start and to deactivate the heating at the end of a preset time.

The spectrophotometer system of apparatus 112 is similar to that of apparatus 12 of the preferred embodiment. Light emitting source 130a emits light in the direction of arrow 1 and detector 135a detects emitted or scattered light traveling in the direction of arrow 2. Light emitting source 130b emits light in the direction of arrow 4 and detector 135b detects emitted or scattered light traveling in the direction of arrow 5. Light emitting source 130c emits light in the direction of arrow 3 and detector 135 detects light traveling in the direction of arrow 3. The spectrophotometer system also includes spectrophotometer controller 194 for controlling the operation of light sources 130a,b,c and detectors 35a,b,c, and power source 190.

Referring now to FIG. 8-13, illustrated therein is a preferred embodiment of the quantitative analysis method of the present invention.

The quantitative analysis method of the present invention is based on the recognition that there is a relationship between initial population and growth population with time. The time interval between the start of the test (starting population) and a fixed growth population is a function of the initial population, the incubation temperature and the growth media. Thus keeping the incubation temperature and growth media as constants, the time required to reach the fixed growth population is a direct function of the initial population.

A chromogenic/fluorogenic reagent such as Readycult® (Merck KgaA) or Colilert® (IDEXX) provides the mechanism by which the microbial growth population (total coliform and E. coli) can be monitored and measured in this invention through photometric detection process. The specific enzymes produced by these organisms (for example β-galactosidase (total coliform) and β-glucuronidase (sec to E. coli)) will metabolize the nutrient-indicator and releases the chromophor or fluorophor into the liquid medium. The concentration of the chromophors or flurophors, at a given time, in the detection medium is proportional to the growth population at that time and hence the change in the signal intensity due to the increase in concentration of the colour components is a measure of the time based growth population.

The population detection time ($t_{pop}$), which is defined as the time taken to reach a detectable population size, has been used to estimate bacterial growth parameters. The detection time has been shown to be inversely proportional to the logarithm of the inoculum (initial population of the microbe) level.

$$t_{pop} \propto 1/\log X_0 \quad \{1\}$$

where $X_0$=initial bacterial population

The time of significant deviation (TSD) is the time at which the measured photometric signal quantity above the baseline signal is statistically significant. TSD also depends on the initial concentration of the bacteria in the sample and higher the initial bacterial count shorter the TSD. Since the increase in population size can be measured using increase in signal output, the time required to obtain a significant deviation (TSD) of the signal output from the baseline should correspond to $t_{pop}$ if measured in the growth phase. The method is $$t_{pop} = TSD \quad \{2\}$$

And therefore, $$TSD \propto 1/\log X_0 \quad \{3\}$$

This linear correlation curve equation—LCCE between TSD and initial population of the microbe under investigation ($X_0$) provides, in addition to detecting the presence, quantitative information of the bacterial population.

Figure 8:
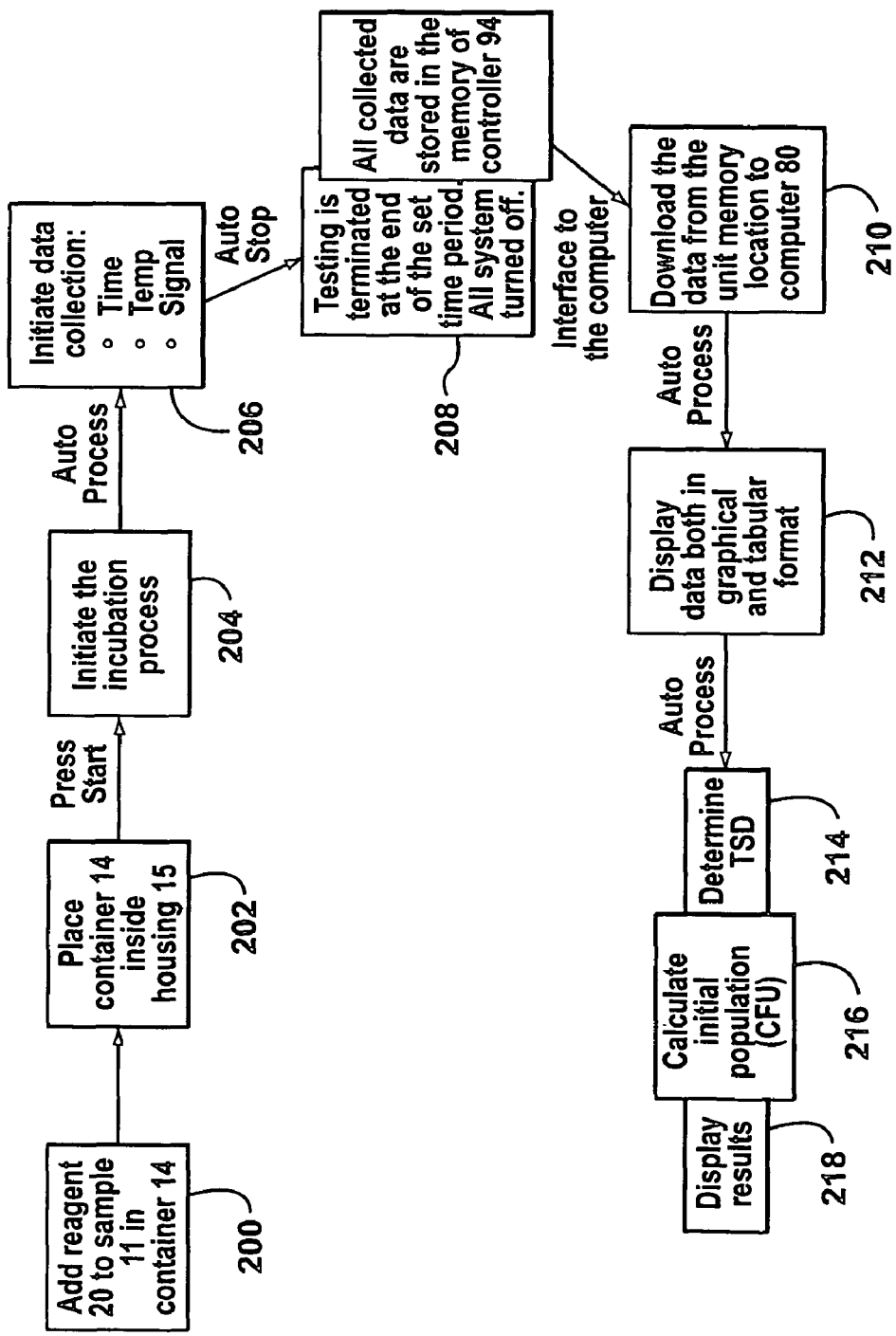
FIG. 8 is a flow chart illustrating the method of the subject invention.
Figure 9:
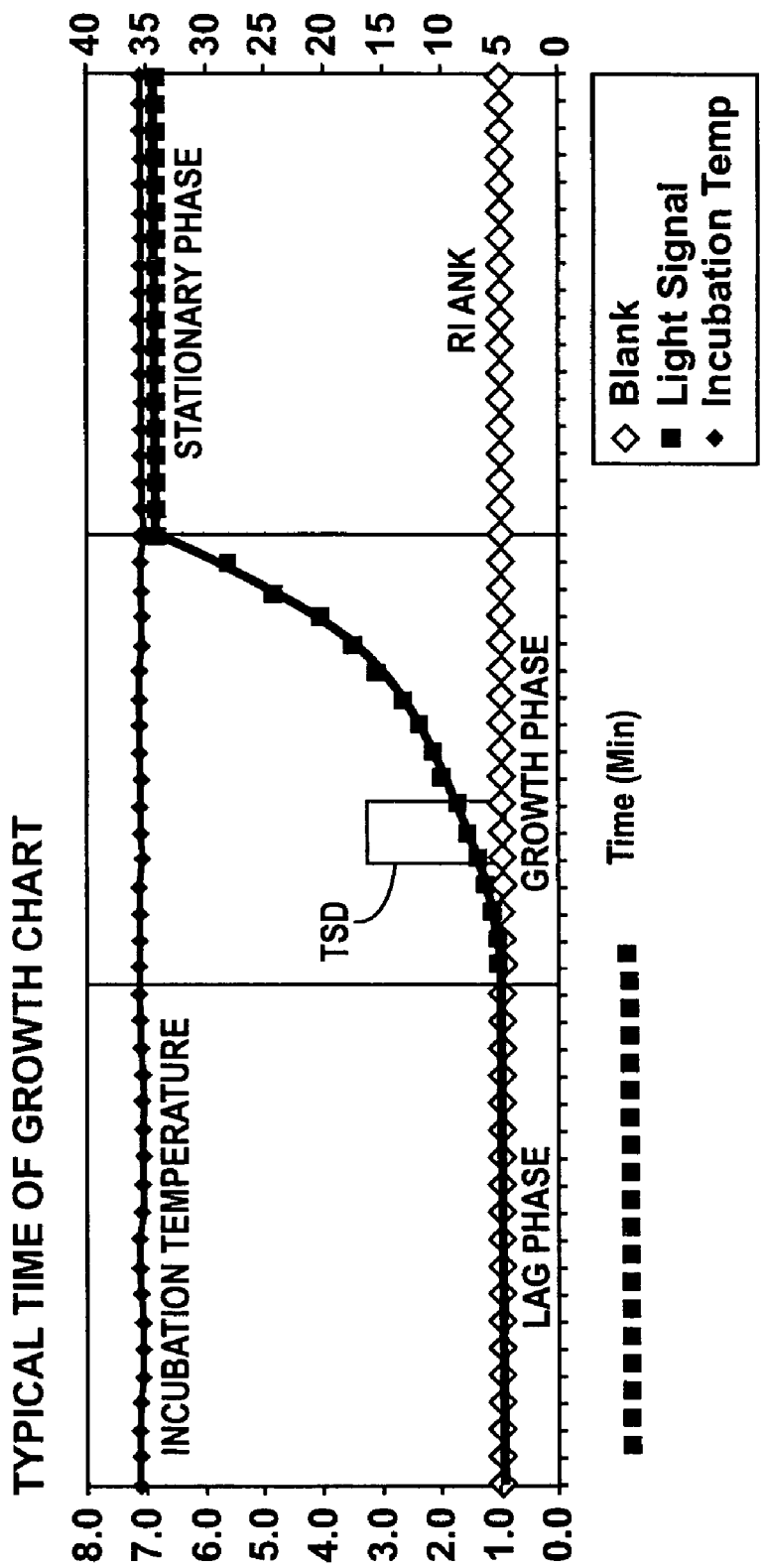
FIG. 9 is a graph illustrating a typical time of growth curve.

FIG. 8 is a flow chart describing the steps of the subject method. At block 200, reagent 20 is mixed with liquid sample 11 having an unknown initial population of a microbiological material in specimen container 14, thereby creating a sample/reagent mixture. Reagent 20 provides a detectable parameter, such as colour or fluorescence, indicative of the microbiological material. At block 202, specimen container 14 is placed inside housing 15 and cap 50 is placed on housing 15. At block 204, the incubation process is initiated, and the sample/reagent mixture is incubated in the enclosed housing at a constant temperature over a period of time.

At block 206, data collection is initiated, and the changes in the detectable parameter are measured as the sample/reagent mixture is incubated over time. These changes are measured by propagating light of a known intensity within the sample/reagent mixture in specimen container 14, and detecting changes in the intensity of the light over the period of incubation.

During the incubation period, data relating to the time, temperature and photometric signal indicative of the changes in light intensity are collected by spectrophotometer controller 94. An increase in microbial population with time is accompanied by the increase in photometric signal. This generates a real-time microbial growth curve, such as that shown in FIG. 9. At block 208, the testing is terminated, and the collected data is stored in the memory of microprocessor 95 of spectrophotometer controller 94.

Figures 10, 11:
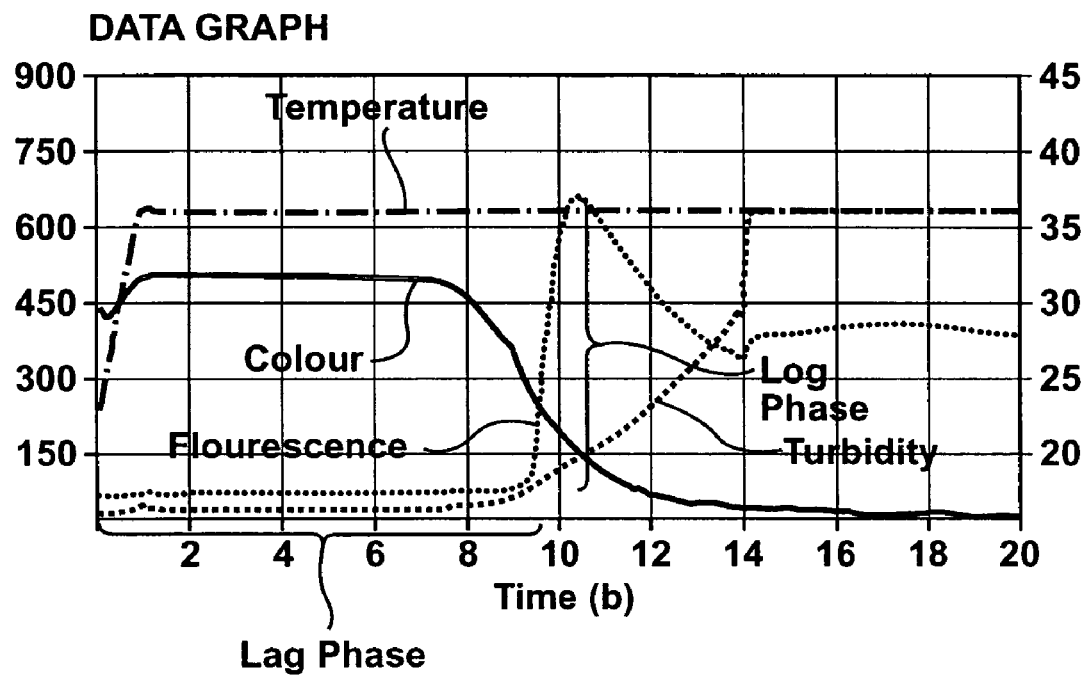
FIG. 10 is a data graph displaying exemplary growth curves for two different microbiological parameters.
FIG. 11 is a data table showing the results generated by the method of the present invention.

At block 210, the data is downloaded to external data recorder 80, preferably computer 85 installed with custom software. At block 212, computer 80 processes the data and displays the result both in graphical format and tabular format. FIG. 10 illustrates the growth curves of all selected parameters of a typical sample, as recorded on a real time basis or downloaded from apparatus 12, as well as the incubation temperature profile. The left hand side vertical values indicate signal intensity (arbitrary numbers). The right hand side is the temperatures in ° C. (Celsius). The bottom horizontal scale represents the time in hours. FIG. 11 illustrates a data table that contains the values of the parameter signals along with the time and temperature for a typical sample.

Figure 12:
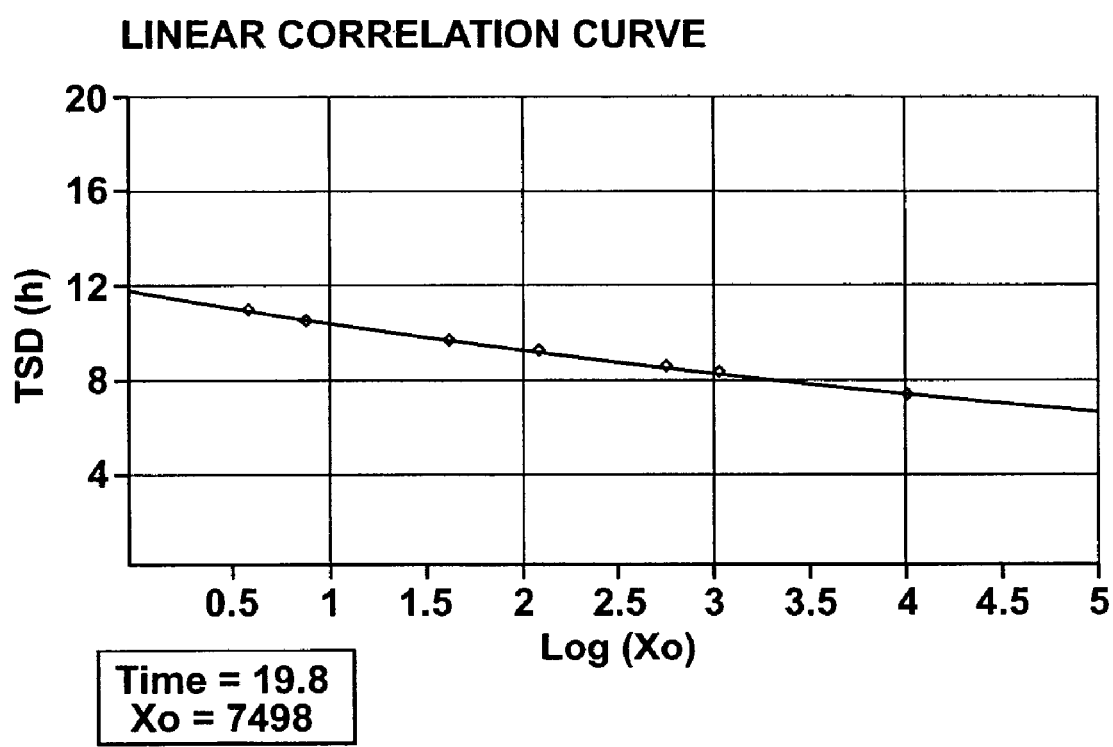
FIG. 12 is an exemplary linear correlation curve used in the method of the subject apparatus.

At block 214, the software of computer 85 automatically calculates the TSD based upon a pre-set value of the photometric signal above the baseline signal value defined by the analyst. At block 216, a built in pre-defined linear correlation curve equation is used to calculate the initial population (expressed in Colony Forming Unit (CFU) in a given sample volume) of the microbial parameter under investigation. To obtain this linear correlation curve equation, a series of split samples of varying initial microbial population (for example E. coli) are run both using the method of the present invention and a standard method (Membrane Filtration). The pre-defined linear correlation curve equation (LCCE) is generated by plotting TSO values obtained from the present invention and the corresponding initial population values ($X_0$) from the membrane filtration method. A sample linear correlation curve is shown in FIG. 12.

Figure 13:
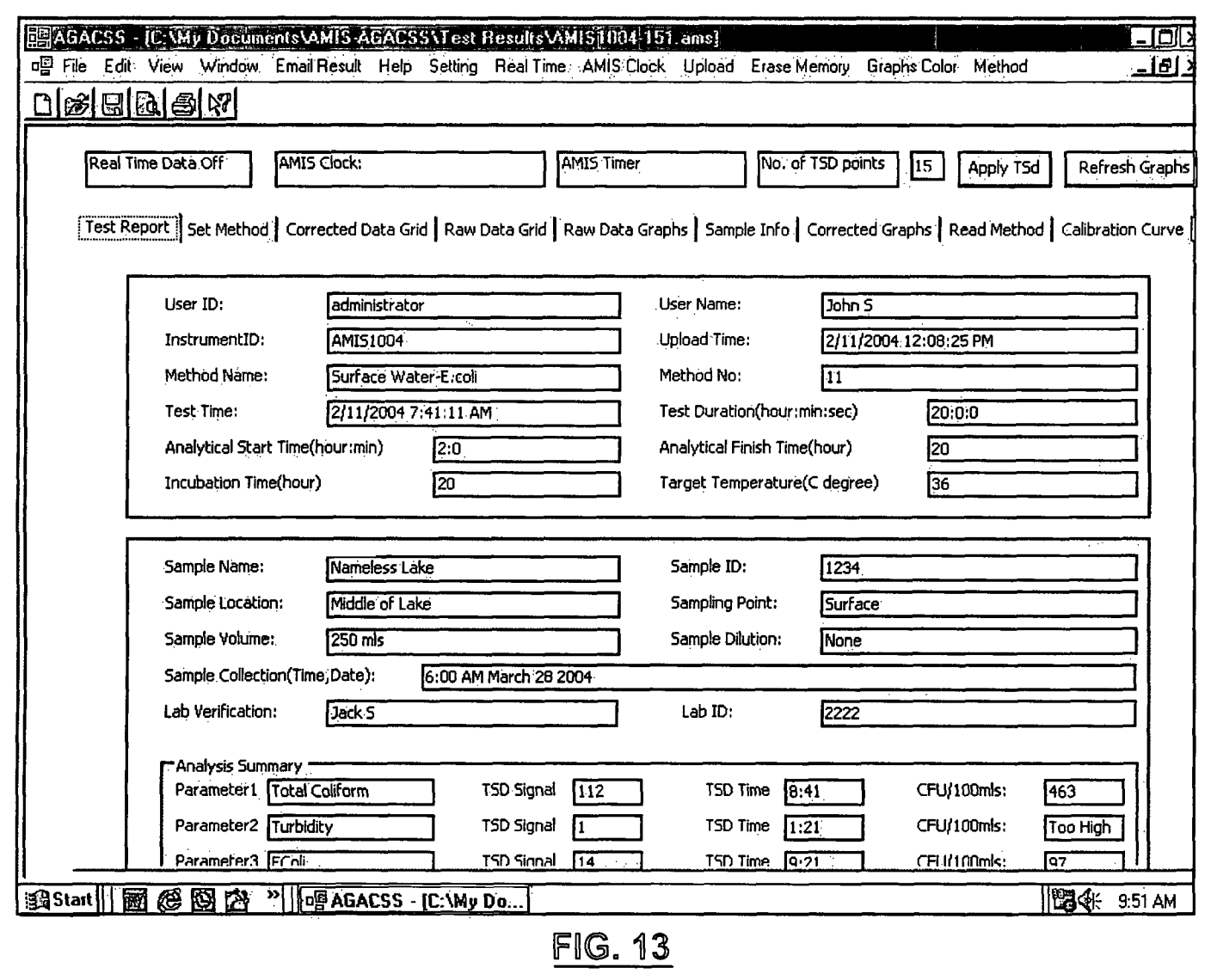

At block 218, the initial population values are displayed on a computer screen such as that shown in FIG. 13.

The method of the present invention accordingly provides a continuous, non-intrusive monitoring and recording of one or more detectable parameters as the incubation process progresses. A significant deviation of the output signal is an indication of the presence of the detectable parameter, while the time taken to reach the significant deviation provides a quantitative analysis of the parameter.

Figure 14A:
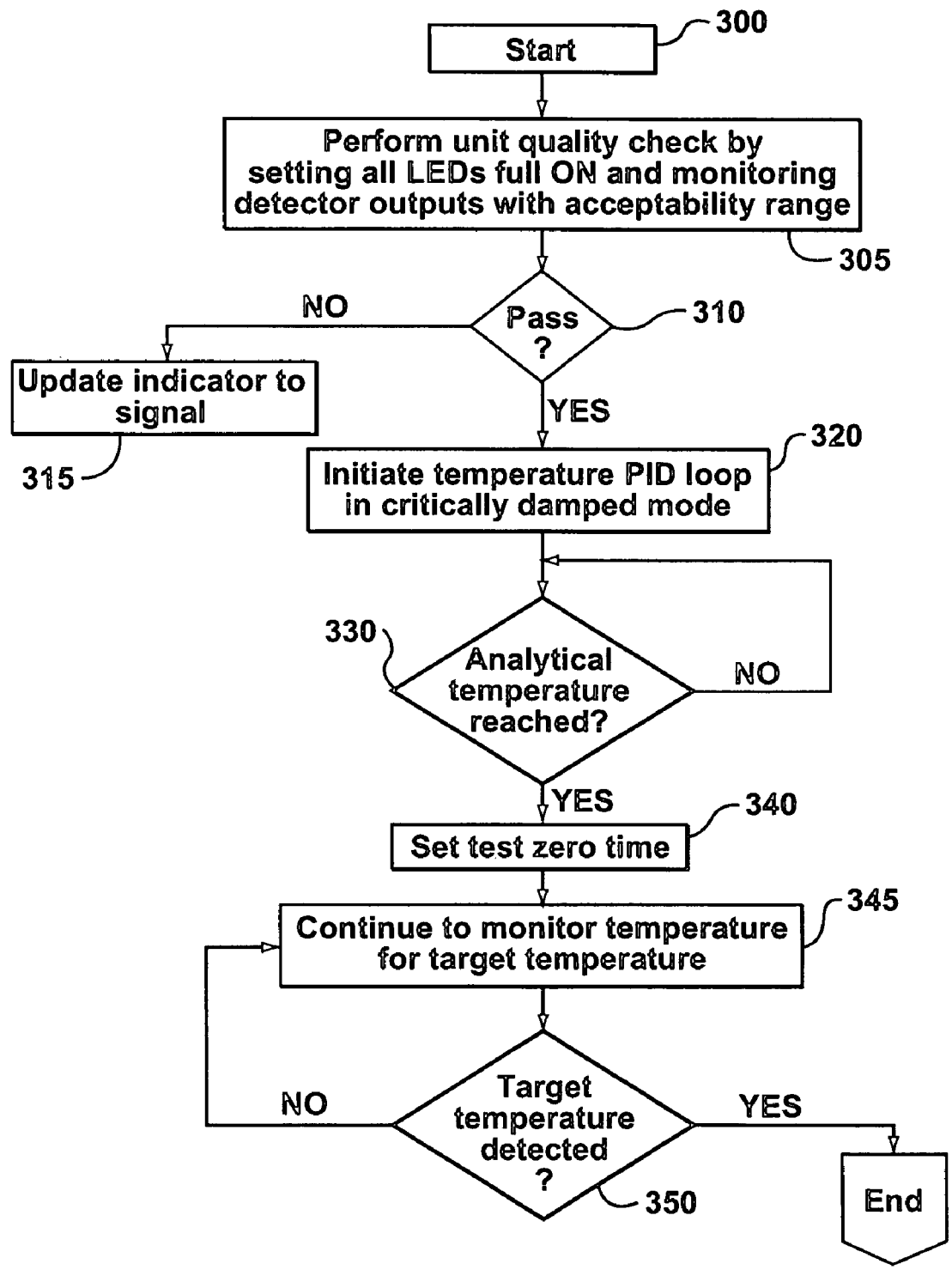
FIG. 14a is a flow chart illustrating the heating control algorithm of the present invention.
Figure 14B:
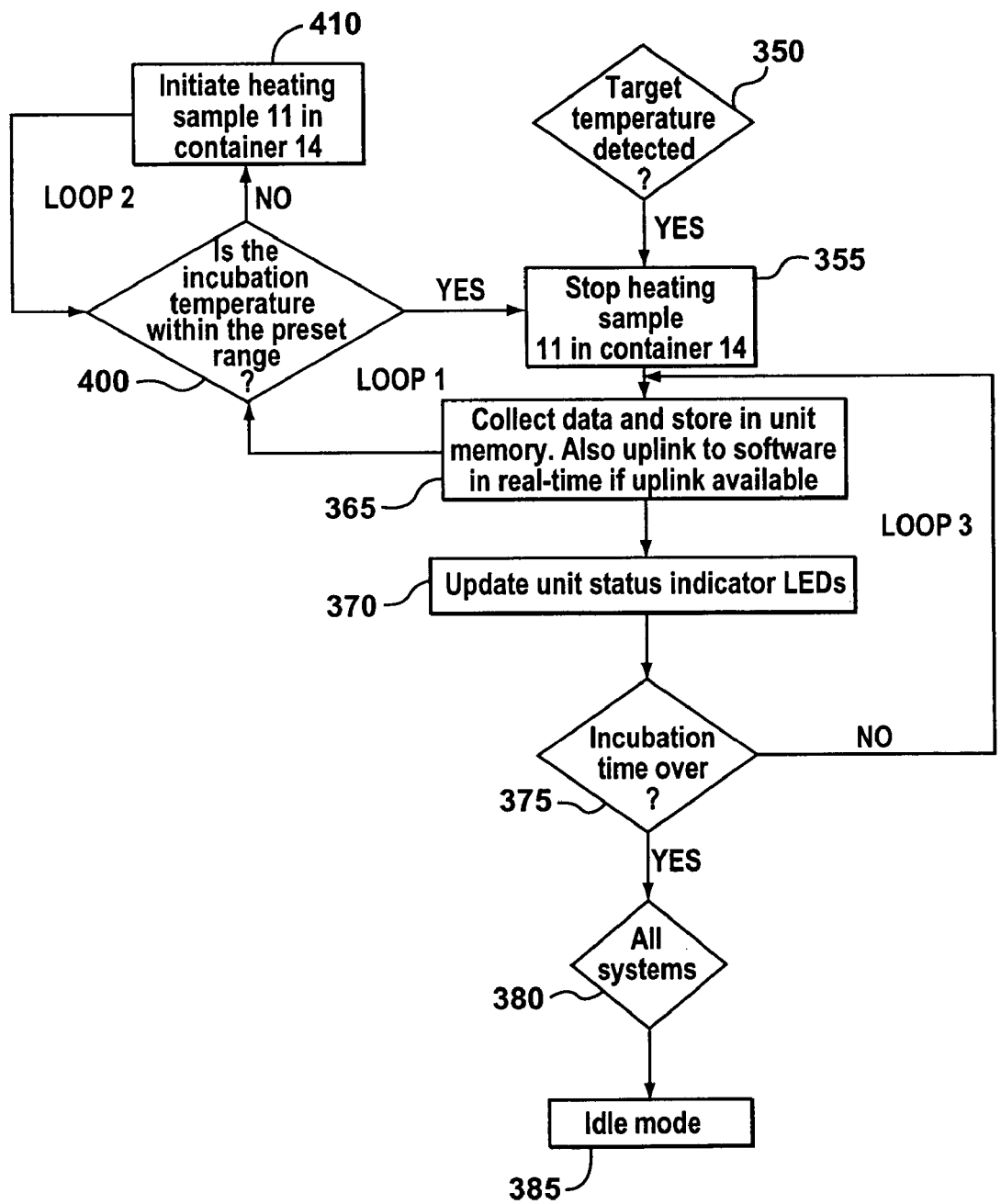
FIG. 14b is a flow chart illustrating the temperature control and data collection algorithm of the present invention.

Referring now to FIGS. 14a and 14b, illustrated therein are the heating and temperature control and data collection algorithms of controller 92 and 94. Pressing the power switch 13 at the command block 300 initiates the controller 92 program.

At command block 305 the controllers 92 and 94 perform a quality check to verify the incubation and detection systems and components are functioning properly.

At command block 310 if the logic is "Yes" the controllers 92 and 94 will proceed to block 320. If the logic is "No" the controllers will initiate the appropriate LEDs to signal "Failed Unit".

At command block 320 the controller 92, through heating element 24, heats the sample 11 in container 14 and at a pre-determined interval monitors the temperature of the sample 11 through temperature sensor 25.

If the logic at command block 330 is "No" then the controller 92 continues heating and monitoring the temperature of sample 11 in container 14.

If the logic at command block 330 is "Yes" then the temperature of the sample 11 has reached a pre-determined temperature value as measured by the temperature sensor 25. The controller 92 will then set the test time zero and continue monitoring the temperature of the sample 11 in container 14. The controller 92 also starts monitoring the time.

If the logic in command block 350 is "No", the controller 95 will continue heating and monitoring the temperature of sample 11.

If the logic in command block 350 is "Yes", the controller 92 moves to block 355 and stops heating sample 11 in container 14 and moves to command block 365.

At command block 365 controller 92 starts collecting temperature and time data while controller 94 starts collecting the signal data. Controller 92 also initiates the temperature control Loop 1 to maintain the incubation temperature at the preset range. If the logic at block 400 within Loop 1 is "Yes" then the controller falls back to block 355 and continues the loop.

If the logic at block 400 is "No" then the controller will go to command block 410 and initiate heating of sample 11 in container 14. Loop 2 will continue until the logic at block 400 becomes "Yes" and falls back to Loop 1.

Irrespective of the logic loops 1 and 2, both controllers 92 and 94 will collect their respective data at a pre-set time interval and store the data in the processor memory.

At block 370 the status LEDs 97 are updated to indicate the test in progress.

If the logic at command block 375 is "No" the controllers 92 and 94 will go back to command block 365 and continue collecting data, thus initiating a data collection loop—Loop 3. If the logic at block 375 is "Yes" then the test is deemed completed and the controllers 92 and 94 stop monitoring and collecting data and shut down both incubation and detection systems and go into idle (stand by) mode at command block 385 and await further instruction from the user or analyst.

The methods and apparatus of the subject invention provide a number of advantages over standard membrane filtration methods. The subject methods and apparatus provide for a rapid but simple, reliable and accurate onsite testing of microbiological material in various types of liquid samples, including drinking water and recreational water. Other advantages include less interference from turbidity, no need for dilution because of large dynamic analytical range, simplified operation through total automation, and build in quality control (QC) providing auto QC for every test.

It should be appreciated that various modifications can be made to the embodiments of the methods and apparatus described herein. While the spectrophotometer system of the preferred embodiment comprises three spectrophotometers, it should be understood that the apparatus could comprise a different number of spectrophotometers. As well, the spatial configuration of the source-detectors could be altered significantly without departing from the present invention. Also, each spectrophotometer can be configured for detecting different test parameters and can be operated independently or simultaneously.

It should also be appreciated that the light emitting sources are not limited to LEDs (as they could be lasers, or laser diodes), and the detectors are not limited to phototransistors, (as they could be photodiodes, photoresistors, CCDs, etc.)

Furthermore, the method of the present invention is not limited to the detectable parameters of the preferred embodiment, as the present method could be used to detect light emission resulting from bioluminescence or chemiluminescence processes resulting from a biological or chemical component in reagent 20 within the sample container 14. This would allow the method and apparatus of the present invention to be used for toxicity studies using bioluminescence bacteria.

Also, the light emitting source and the detector of any or all of the spectrophotometers could be placed outside of the incubation-detection chamber 65 but within apparatus 10 and used to monitor the signal growth through fiber optics placed strategically within the chamber 65.

Accordingly, various modifications can be made to the embodiments of the invention described and illustrated herein without departing from the present invention, the scope of which is defined in the appended claims.

The invention claimed is:

1. An apparatus for rapid analysis of microbiological materials in a liquid sample, comprising:
    (a) a specimen container for containing a liquid sample, the specimen container being made from a material that allows for propagation of light;
    (b) a housing having an incubation chamber shaped for holding the specimen container, the housing comprising a container holder mounted within the incubation chamber, the container holder being configured to hold the specimen container, and wherein the housing comprises a base, and the container holder comprises an upwardly extending, generally cylindrical wall mounted on the base, the wall having an open top end shaped for receiving the specimen container and a removable cap removably coupled to the base, the removable cap being shaped to surround and enclose the container holder;
    (c) a heating element mounted within the container holder for incubating any microbiological materials within the liquid sample; and
    (d) one or more light emitting sources and one or more light detectors mounted within the container holder for propagating light within the specimen container and positioned for measuring the light absorbed, emitted or scattered by the liquid sample as the microbiological materials are incubated within the incubation chamber over time, thereby detecting changes in amount of the light as the light propagates through the microbiological materials and producing a detector signal indicative of the changes;
wherein the bottom portion of the wall of the container holder comprises a pair of diametrically opposed indents, and the specimen container comprises a pair of diametrically opposed recesses shaped to register with the indents and wherein at least one light emitting source is mounted in one of the pair of indents, and at least one detector is mounted in the other of the pair of indents to provide a field of view of at a 180° angle to the optical path of the at least one light emitting source.

2. The apparatus defined in claim 1, also comprising a spectrophotometer controller for controlling the light emitting source and the detector, wherein the spectrophotometer controller comprises a microprocessor for processing the detector signal and for generating a record of the changes in the light as a function of time.

3. The apparatus defined in claim 1, wherein the light emitting source comprises a light emitting diode, and the detector comprises a phototransistor.

4. The apparatus defined in claim 1, that comprises a first light emitting source for propagating a first beam of light within the specimen container and a first detector mounted within the container holder for detecting changes in the first light beam, and a second light emitting source for propagating a second beam of light within the specimen container, and a second detector mounted within the container holder for detecting changes in the second beam of light.

5. The apparatus defined in claim 4, further comprising a third light emitting source for propagating a third beam of light within the specimen container and a third detector mounted within the container holder for detecting changes in the third beam of light.

6. The apparatus defined in claim 1, wherein the light emitting source and the detector are mounted in the container holder at a location proximate to the specimen container when the specimen container is placed in the housing.

7. The apparatus defined in claim 1, further comprising a temperature sensor mounted within the container holder.

8. The apparatus defined in claim 7, wherein the temperature sensor extends upwardly into the container holder, and the specimen container has a bottom cavity shaped to accommodate the temperature sensor.

9. The apparatus defined in claim 7, wherein the heating element extends upwardly into the container holder, and the specimen container has a bottom cavity shaped to accommodate the heating element.

10. The apparatus defined in claim 4, also comprising a spectrophotometer controller for controlling the first and the second light emitting sources and detectors so as to detect the changes in the first light beam and the changes in the second light beam at the same time.

11. Apparatus for incubating and analyzing microbiological materials in a liquid sample, comprising:
   (a) a housing comprising a base, a single container holder mounted on the base, the container holder being shaped for holding a specimen container wherein the container holder comprises an upwardly extending generally cylindrical wall mounted on the base, and a bottom portion of the wall comprises a pair of diametrically opposed indents and wherein the specimen container comprises a pair of diametrically opposed recesses shaped to register with the indents, and a removable cap releasably coupled to the base, the removable cap being configured to surround and enclose the container holder so as to create an insulated and light tight incubation-detection chamber for the specimen container;
   (b) heating apparatus for heating and maintaining the liquid sample at a constant temperature, the heating apparatus comprising a heating element mounted within the container holder and a temperature sensor mounted within the container holder; and
   (c) at least one light emitting source mounted within the container holder in one of the pair of indents for propagating light within the specimen container and at least one light detector mounted within the container holder in the other of the pair of indents and positioned to have a field of view at a 180° angle to the optical path of the at least one light emitting source for measuring the light absorbed, emitted or scattered by the microbiological materials as the liquid sample is maintained at the constant temperature within the incubation-detection chamber over time and for producing a detector signal indicative of changes in the measured light.

12. An apparatus for rapid analysis of microbiological materials in a liquid sample, comprising:
   (a) a housing having an incubation chamber shaped for holding a specimen container for containing a liquid sample, the specimen container being made from a material that allows for propagation of light, the housing comprising a container holder mounted within the incubation chamber, the container holder being configured to hold the specimen container wherein the container holder comprises an upwardly extending generally cylindrical wall mounted on the base, and a bottom portion of the wall comprises a pair of diametrically opposed indents;
   (b) a heating element mounted within the container holder for incubating any microbiological materials within the liquid sample; and
   (c) at least one light emitting source mounted within the container holder in one of the pair of indents for emitting light within a liquid sample in the specimen container and at least one light detector mounted within the container holder in the other of the pair of indents and positioned to have a field of view at a 180° angle to the optical path of the at least one light emitting source for measuring the light absorbed, emitted or scattered by the liquid sample as the microbiological materials are incubated within the incubation chamber over time.

* * * * *